Figure 1:
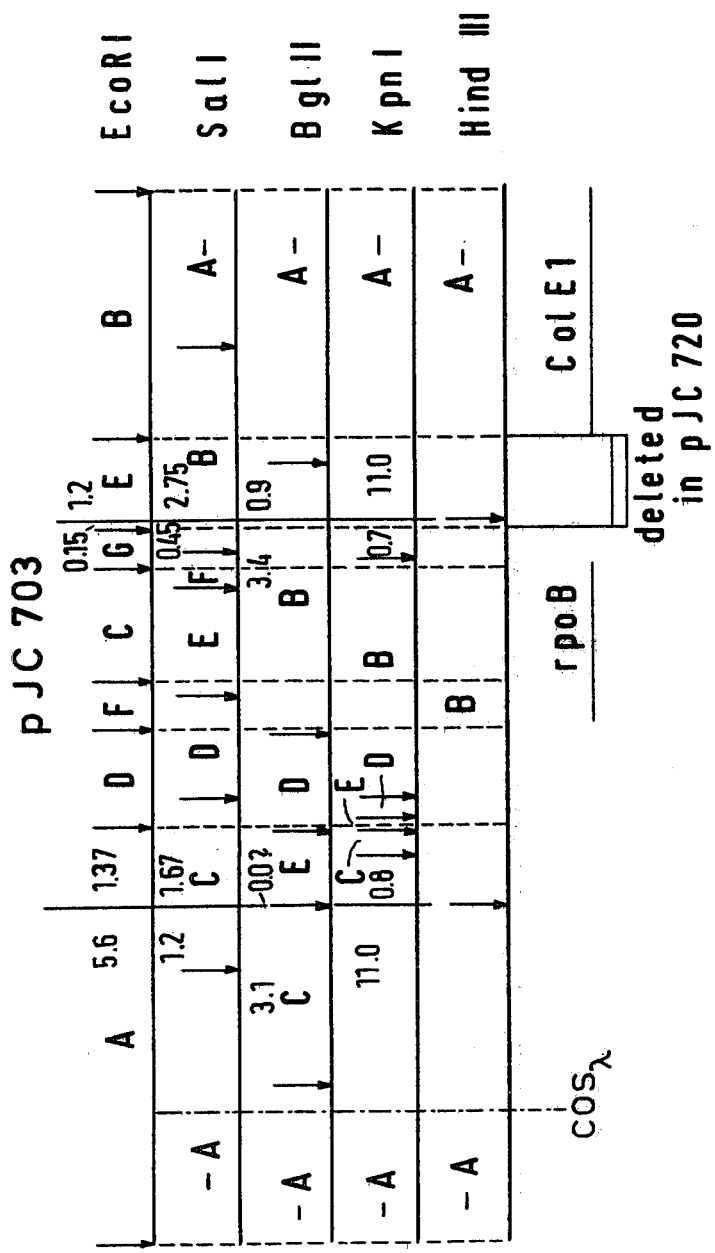

United States Patent [19]

Collins et al.

[11] 4,304,863
[45] Dec. 8, 1981

[54] PROCESS FOR THE PRODUCTION OF HYBRID BACTERIA

[75] Inventors: John Collins, Brunswick, Fed. Rep. of Germany; Barbara Hohn, Basel, Switzerland

[73] Assignee: Gesellschaft für Biotechnologische Forschung mbH, Braunschweig-Stöckheim, Fed. Rep. of Germany

[21] Appl. No.: 25,719

[22] Filed: Mar. 30, 1979

[30] Foreign Application Priority Data

Mar. 31, 1978 [DE] Fed. Rep. of Germany ....... 2814039

[51] Int. Cl.$^3$ ............................................ C12N 15/00
[52] U.S. Cl. ..................................... 435/172; 435/68; 435/317
[58] Field of Search ............................... 435/172, 317

[56] References Cited

PUBLICATIONS

Collins, Current Topics in Microbiology & Immunology, vol. 78, pp. 121–170, (1977).
Hohn et al., Proc. Natl. Acad. Sci. USA, vol. 74, No. 8, pp. 3259–3263, Aug. 1977.
Garland et al., Biochemistry of Genetic Engineering, Biochemical Society Symposium No. 44, held Jul. 1978, (1979).
Clewell & Helinski, Biochem 9, (1970), pp. 4428–4440.
Collins, Fiil, Jorgensen & Friesen, "Control of Ribosome Synthesis", Alfred Benzon Symposium IX, Munksgaard, 1976, pp. 356–369, Maaløe & Kjieldgaard Ed., Copenhagen.
Nichols & Donelson, J. of Virology, vol. 26, No. 2, (1978), pp. 429–434.
Cohen, Chang, Boyer & Helling, Proc. Nat. Acad. Sci. USA, vol. 70, No. 11, (1973), pp. 3240–3244.
Collins & Brüning, Gene 4, (1978), pp. 85–107.
Hohn & Katsura, "Current Topics in Microbiology & Immunology", vol. 78, (1977), pp. 92–94.
Bachmann, Low & Taylor, Bacteriol. Rev., 40, (1976), pp. 116–167.
Collins & Hohn, Proc. Nat. Acad. Sci. USA, vol. 75, (1978), pp. 4242–4246.
Emmons, MacCosham & Baldwin, J. Mol. Biol, (1975), vol. 91, pp. 133–146.
Hershey, "The Bacterophage Lambda", Publ. Cold Spring Harbor Lab., (1971), pp. 773–779.
Novick, Clowes, Cohen, Curtiss, Datta & Falkow, Bacteriological Reviews, Mar. 1976, pp. 168–189.
Collins et al., Microbiology, 1978, Amer. Soc. for Microbiology, Washington, pp. 150–153.
Hohn & Hohn, Proc. Nat. Acad. Sci. USA, vol. 71, (1974), pp. 2372–2376.
Roberts, CRC CRit. Rev. Biochem. 4, (1976), pp. 123–164.
Morrison, J. Bact., 132, (1977), pp. 349–351.
Feiss et al., Virology 77, (1977), pp. 281–293.
Blohm, Proc. 2nd Int. Symp. Microbiol. Drug Resist., vol. 2, Tokyo, 1977.
Clarke & Carbon, Cell. 9, (1976), pp. 91–99.
Emmons, J. Molec. Biol., 93, (1974), pp. 511–525.
Thomas et al., Proc. Nat. Acad. Sci. USA, 71, (1974), pp. 4579–4583.
Murray & Murray, Nature, 251, (1974), pp. 476–481.
Murray et al., Molec. Gen. Genet., 150, (1977), pp. 53–61.
Blattner et al., Science 196, (1977), pp. 161–169.
Cameron et al., Proc. Nat. Acad. Sci. USA, 72, (1975), pp. 3416–3420.
Sternberg et al., Gene, 1, (1977), pp. 255, 280.

*Primary Examiner*—Alvin E. Tanenholtz
*Attorney, Agent, or Firm*—Hammond & Littell, Weissenberger and Muserlian

[57] ABSTRACT

The present invention is directed to a process for the production of hybrid bacteria, characterized in that
  (a) a hybrid plasmid having only one cos site of a lambda or a lambdoid phage is produced from (1) a bacterial plasmid of not more than 21 Megadaltons and having only one cos site of a lambda or a lambdoid phage and (2) a foreign DNA fragment,
  (b) the resulting hybrid plasmid is packaged with the lysate of a lambda or lambdoid phage and
  (c) the packaging product is transduced into *Escherichia coli* whereby hybrid bacteria are formed.

4 Claims, 1 Drawing Figure

PROCESS FOR THE PRODUCTION OF HYBRID BACTERIA

The possible technical applications of so-called gene technology are enormous if the possibility is taken into consideration of introducing DNA from any source (from, for example, bacteria, yeast, fungi, animals and human beings) into (different) bacteria. As a result of progress made in the DNA chemistry and the molecular genetics of *Escherichia coli* it is likely that it is only a question of time to apply the DNA transplantation technology to the production of hybrid bacteria which are able to produce products of economic interest due to the presence of foreign DNA. The production of, for example, a human hormone or a fungus antibiotic with a bacterium like *Escherichia coli* which can easily be cultivated and fermented is of enormous technical interest.

Collins gives a review of the known transformation process in Current Top. Microbiol. Immunol., 78 (1977) 121–170, 129. Hohn and Murray describe in Proc. Nat. Acad. Sci. USA 74 (1977) 3259–3263 a packaging of DNA of phage lambda and lambdoid phages (which have been combined with foreign DNA fragments in vitro) for the in vitro production of new hybrids. There follows a scheme of the said new systems:

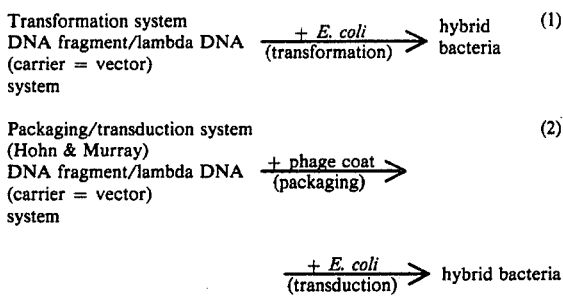

These known systems, however, have not been satisfactory with respect to their efficiency.

The invention starts from the problem of how to provide a process having a better efficiency.

This problem is solved according to the invention by a process for the production of hybrid bacteria which is characterized in that (a) a bacterial plasmid of not more than about 21 Megadaltons and having one or several cos sites of phage lambda or a lambdoide phage and only one cut site per restriction endonuclease is cut in the presence of one or two restriction endonucleases, (b) the cut plasmid is coupled with a DNA fragment in the presence of a ligase to give a hydrid plasmid, (c) the resulting hybrid plasmid is packaged with the lysate of phage lambda or a lambdoide phage and (d) the packaging product is transduced into Escherichia coli whereby hybrid bacteria are formed.

The term plasmid was explained by Collins in Current Top. Microbiol. Immunol. 78 (1977) 121–170 on page 122 in greater detail; additional quotations are mentioned. The expert is familiar with the production of plasmids; it can be carried out according to, for example, Clewell & Helinsky, Biochem. 9 (1970) 4428–4440 or in an analogous manner. The expert can apply usual analytical methods, for example, the gel electrophoresis, to examine the plasmid size; see, for example, Collins, Current Top. Microbiol. Immunol., 78 (1977) 121–170, FIGS. 3 to 5 on pages 140 to 142.

With respect to the phage lambda the cos site means that area which comprises the cohered cohesive ends. The process according to the invention uses only plasmids into which this area has been inserted so that these plasmids comprise cos sites too. Without any cos site plasmids cannot be packaged. With respect to the production of plasmids having cos sites (so-called cosmids) it is possible to apply the process according to Collins, Fiil, Jørgensen & Friesen in Control of Ribosome Synthesis, Alfred Benson Symp. IX, Munksgaard, 356–369, Maaløe & Kjeldgaard, Ed., Copenhagen 1976, or analogous processes; the cos site is designated in m'm in FIG. 3 in the publication mentioned. With respect to a control of presence and number of cos sites cf., for example, Nichols & Donelson, J. Virology, 26 (1978) 429–434. It goes without saying that cosmids can be used for the process of the invention which are derived from cosmids which have been produced according to known or analogous methods.

With respect to the prior art of restriction enzymes attention is drawn to, for example, Roberts, CRC Crit. Rev. Biochem., 4 (1976) 123–164. The experts are familiar with the application of restriction endonucleases; see for example, Cohen, Chang, Boyer & Helling, Proc. Natl. Acad. Sci. USA, 70 (1973) 3240–3244, and Collins, Current Top. Microbiol. Immunol., 78 (1977) 121–170, especially page 124. It is possible to examine by usual analytical methods, for example, by a gel electrophoresis, whether a plasmid has one or several cut sites with respect to a certain restriction enzyme.

In case of, for example, one cut site only one restriction product is produced, whereas in case of two cut sites two fragments result.

It has been found that some plasmids cannot be cut by certain restriction enzymes at all. However, in order also to use such restriction enzymes in the process according to the invention the following procedure is possible. It is possible to cut a plasmid with a restriction enzyme, which cuts the plasmid at one site only. Parallel therewith a foreign DNA can be cut in such a manner that a DNA fragment results which can be cut at one site by a different restriction enzyme which does not cut the plasmid. Then the foreign DNA fragment can be coupled with the cut plasmid so that a hybrid plasma results which can now be cut by the different restriction enzyme at a certain site.

The foreign DNA fragment which is coupled with a plasmid at step (b) mentioned above, of the process according to the invention, is a fragment which gives the hybrid bacterium to be produced a desired feature.

With respect to the coupling in the presence of a ligase it is possible to use the method according to, for example, Cohen, Chang, Boyer & Helling, Proc. Natl. Acad. Sci. USA, 70 (1973) 3240–3244 or an analogous method. All methods listed by Collins in Current Topics Microbiol. Immunol., 78 (1977) 121–170 on page 126 can be taken into consideration for the production of hybrid plasmids.

Phage lambda or lambdoid phages like Phi 80 can be used for the production of a phage lysate. The production of the phage lysate, the packaging and the transduction can be carried out according to Hohn & Murray, Proc. Nat. Acad. Sci. USA, 74 (1977) 3259–3263 or analogous methods.

The expert may use usual analytical methods to screen the produced hybrid bacteria and to calculate the efficiency of the process according to the invention. In this connection the expert may select a feature of the hybrid bacteria which is suitable for a selection, for example, their resistivity against antibiotics, as for example, rifampicin or ampicillin; preferably, this feature has been coded by the plasmid.

It is possible to carry out the process according to the invention in vitro.

The advantage of the process of the invention in comparison with the known transformation system consists in the fact that in case of a transduction a higher efficiency can be achieved and larger foreign DNA fragments can be transduced, for example, of a size of more than 2, especially 3 and more and preferably 5 Megadaltons and more, the upper limit being dependent on the selected packaging and transducing system. In case of the process according to the invention hybrid plasmid DNA can be introduced into living bacteria at least one hundred times better than in the known transformation systems; in the case of larger hybrid plasmids the process according to the invention can be carried out at least 1,000 to 100,000 times better; cf. Collins loc. cit. 170. The better efficiency in the case of large hybrid plasmids results from the strong counter-selection which occurs in transforming large molecules.

The particular advantage of the process according to the invention over the known packaging/transduction system with lambda vectors is the small size of the plasmid vectors which consequently allows packaging of large foreign DNA fragments.

The surprisingly high proportion of hybrid bacteria which can be achieved in the process according to the invention simplifies the following procedure remarkably whereas the selection and screening steps of the known prior art are complicated in a detrimental manner.

Preferably a plasmid is used having not more than about 18 Megadaltons. In case of such plasmids (and contrary to hybrid plasmids) the packaging and transducing of a plasmid is considerably worse so that an especially strong selection in favor of hybrid plasmids results; cf. Collins & Brüning, Gene 4 (1978) 85–107.

Preferably a plasmid having only one cos site is used. It is surprising that the process according to the invention can be carried out in this case since DNA having one cos site only has been considered as not being packageable, cf., for example, Hohn & Katsura, Current Top. Microbiol. Immunol., 78 (1977), 92, with additional quotations.

With respect to the nomenclature in the field in question attention is drawn to the following publications:

(1) Bachmann, Low & Taylor, Bacteriol. Rev., 40 (1976) 116–167;

(2) Collins, Current Top. Microbiol. Immunol., 78 (1977) 121–170;

(3) Collins & Hohn, Proc. Nat. Acad. Sci. 75 (1978) 4242–4266;

(4) Emmons, Maccosham & Baldwin, J. Mol. Biol. 91 (1975) 133–146;

(5) Hershey, The Bacterophage Lambda, Publ. Cold Spring Harbor Lab. (1971) 773–779.

(6) Novick, Clowes, Cohen, Curtiss, Datta & Falkow, Bacteriol. Rev., 40 (1976) 168–189;

(7) Roberts, CRC Crit. Rev. Biochem. 4 (1976) 123–164.

| Abbreviations used | Quotations No. | page |
|---|---|---|
| ATP (= adonosine-5'-triphosphate) | | |
| (lambda) b2 | 5 | 779 |
| Bacto-Tryptone (= protein extract from DIFCO laboratories) | | |
| Bgl II | 7 | 6 |
| CI$_{ts}$ (ts = temperature sensitiveness) | 5 | 778 |
| Col El | 6 | 182 |
| D | 5 | 778 |
| Dithiothreitol (= 1,4-dimercapto-2,3-butanediol) | | |
| E | 5 | 778 |
| EcoRI | 2 | |
| Hind III | 2 | |
| hsm$_K^\pm$ | 1 | 130, map pos. 98 |
| hsr$_K^\pm$ | 1 | 130, map pos. 98 |
| imm$_{434}$ | 5 | 775 |
| Kpn I | 7 | 11 |
| leu$^\pm$ | 1 | 131 |
| pel$^\pm$ | 4 | 133–146 |
| PFU (= plaque forming unit) | | |
| pro$^\pm$ | 1 | 134 |
| putrescine (= diaminobutane) | | |
| R-Factor | 6 | 172, quotation 19 |
| recA$^\pm$ | 1 | 135 |
| red3 | 5 | 778 |
| rpoB | 1 | 136 |
| S | 5 | 778 |
| (gen) S | 5 | 778 |
| Sal I | 2 | |
| SLysis | 5 | 778 |
| spermidine (= N-(3-aminopropyl)-1,4-butanediamine) | | |
| su$^\pm$ (= spu) | 1 | 137 |
| Tris (= tris-(hydroxymethyl)-amino methane) | | |
| thi$^\pm$ | 1 | 137 |
| thr$^\pm$ | 1 | 137 |

EXPERIMENTAL PART

Plasmids

The experiments were carried out with two plasmids having a size of 17.3 and 16 Md, respectively, and each having only one cos site the plasmids being designated pJC703 and pJC720, respectively. At least one restriction endonuclease cut the larger plasmid (pJC703) at two sites and the smaller plasmid (pJC720) at one site. In addition, a plasmid having a size of 25 Md was used as molecular weight marker (pJC802).

The preparation of the plasmids pJC720 and pJC703 (FIG. 1) has been described by Collins et. al. in Control of Ribosome Synthesis, Alfred Benson Symp. IX, Munksgaard, pp. 356–369, Maaløe & Kjeldgaard Ed., Copenhagen 1976, and Collins et. al. in Microbiology, Am. Soc. Microbiol., Washington 1978.

Bacteria

With respect to bacteria used, their features, place of lodgement and designation of lodgement attention is drawn to Table I.

The Hohn and Murray Packaging System

Embodiment 1

Exogenous DNA was packaged in vitro as described by Hohn and Murray, Proc. Nat. Acad. Sci. USA 74 (1977) 3259–3263 with the following slight modifications; single colonies of the strains N205=BHB 2690 and N205=BHB 2688 were streaked out on LA plates and grown overnight at 30° C.; with respect to the LA plates, cf. Hohn & Hohn, Proc. Nat. Acad. Sci. USA, 71 (1974) 2372-2376. In addition, control samples were applied onto plates to check temperature sensitivity at 42° C. Single colonies were inoculated into warmed LB medium at an optical density at 600 mm (O.D.$_{600}$) of not more than 0.15 and incubated with shaking until an O.D.$_{600}$ of 0.3 was reached; with respect to the LB medium, cf. Hohn & Hohn, loc. cit. Induction of the p r o phages was effected by incubation of the cultures at 45° for 15 min., standing. Thereafter they were transferred to 37° C. and incubated for 3 additional hours with rigorous aeration. (A small sample of each culture, which was lysis-inhibited as a result of the mutation in gene S, was checked for induction: upon addition of a drop of chloroform the culture cleared.) The two cultures were then mixed, centrifuged at 5,000 rpm for 10 minutes and resuspended at 0° C. in one fivehundredth the original culture volume in complementation buffer (40 mM Tris-HCl, pH 8.0, 10 mM spermidine hydrochloride, 10 mM putrescine hydrochloride, 0.1% mercaptoethanol, 7% dimethyl sulphoxide, the buffer being made 1.5 mM in ATP). Destruction of biological activity of endogenous DNA can be effected by UV irradiation prior to concentration. This cell suspension was distributed in 20 μl portions in 1.5 ml plastic centrifuge tubes (polyallomer from Eppendorf), frozen in liquid N$_2$ and stored at −60° C.

was centrifuged off and the solution used as a phage suspension.

Transduction was carried out by adding 0.4 ml of this phage suspension to 1 ml of N205 or pel$^-$ cells (late exponential culture, i.e. early stationary phase, O.D.$_{600}$ =2.0) in L broth-maltose (1% Bacto-Tryptone (from DIFCO Laboratories), 0.5% yeast extract (from Oxoid), 0.5% NaCl, 0.4% maltose. For the experiment with Pseudomonas DNA, HB101 was used as recipient. After allowing 10 min absorption at 30° the mixture was diluted twenty-fold in fresh L broth and incubated for two hours at 30° C. to allow expression of rifampicin resistance; cf. Morrison, J. Bact., 132 (1977) 349-351, for examination of rifampicin resistance.

Embodiment 2

The packaging mixture contained heat induced *E. coli* N205=BHB 2690 and N205=BHB 2688 in the following buffer: 40 mM Tris-HCl, pH 8.0, 10 mM spermidine hydrochloride, 10 mM putrescine hydrochloride, 0.1% mercaptoethanol, 7% dimethyl sulphoxide. This mixture had been distributed in 20 μl portions in 1.5 ml capped plastic centrifuge tubes (Eppendorf), frozen in liquid nitrogen, and stored up to 2 months at −65° C. Just before use the mixture was transported in liquid nitrogen to the bench. The mixture was placed in ice for about 3 minutes and 1 μl 38 mM ATP added to the still frozen mixture. A few seconds later the ligated DNA sample (from 1 to 15 μl, usually 5 μl) was added and

TABLE I

| strain | features | place of lodgement | designation of lodgement |
|---|---|---|---|
| (i) *Escherichia coli* | | | |
| N205 = BHB 2690 | K 12 strain; hsr$_k$+, hsm$_k$+, recA$^-$, su$^-$; (lambda imm$_{434}$ CI$_{ts}$b2 red3 Eam4 Sam7)/lambda | DSM Göttinger | 1450 |
| N205 = BHB 2688 | K 12 strain; hsr$_k$+, hsm$_k$+, recA$^-$, su$^-$; (lambda imm$_{434}$ CI$_{ts}$ b2 red3 Dam 15 Sam 7)/lambda. | DSM Göttingen | 1451 |
| 5K | hsr$_k$$^-$, hsm$_k$+, thr$^-$, thi$^-$ | DSM Göttingen | 1454 |
| HB 101 | hsr$_k$$^-$, hsm$_k$$^-$, leu$^-$, pro$^-$, recA$^+$ | DSM Göttingen | 1452 |
| GL pel 21W 3 101 | cf. Emmons et. al., J. Mol. Biol., 91 (1975) 133-146 | DMS Göttingen | 1453 |
| CC 703 | } cf. Collins et. al. in Control of Ribosome Synthesis, loc. cit. p. 357 | DSM Göttingen | 1449 |
| CC 720 | | DSM Göttingen | 1448 |
| (ii) *Pseudomonas spec.* | | | |
| AM 1 | | NCIB | 9133 |

The packaging was carried out in the following manner. When needed, one of the said cell suspension samples was transferred in liquid nitrogen and put on ice. Immediately on thawing (3 to 4 minutes on ice), the DNA to be packaged (the hybrid cosmid; 0.01 to 0.2 μg) was added in a volume of 1 to 5 μl. The DNA (the hybrid cosmid) was usually added in the ligation buffer in which it had just been ligated. The solutions were carefully mixed as they thawed and bubbles removed by a few seconds centrifugation in a desk-top centrifuge (from Eppendorf). The mix was incubated 30 min at 37° C. At the end of this incubation period, 20 μl of a frozen and thawed packaging mix, that had been made 0.01 M in MgCl and to which a final 10 μg/ml DNAse was added was mixed to each sample and incubation continued for 20-60 min in 0.5 ml of SMC buffer; with respect to the buffer cf. Hohn & Hohn, loc. cit. A drop of chloroform was added. After mixing, denatured material mixed during the thawing which takes place immediately. The amount of DNA added per 20 μl packaging mixture was usually 1 μg, but increasing this to 4.5 μg still gave approximately the same hybrid yield per μg DNA. After incubation of the packaging mixture at 37° C. (or 25° C.) for 30 minutes, DNA'se was added (10 μg/ml) and MgCl$_2$ (10 mM). When the thick pellet was again liquid (2 to 10 minutes at 37° C.) 0.5 ml of the same buffer as in embodiment 1 and a drop of chloroform were added. After two minutes centrifugation at 5,000 g the supernatant was removed and used as a bacteriophage suspension for transduction of *E. coli* HB101, which had been grown to late exponential phase (O.D.=1.0) in L-broth containing 0.5% maltose. Plating and selection were carried out as described for embodiment 1.

Transformation

Transformation was carried out in strain 5 K. Cultures grown to an $O.D._{600}$ of 0.5 were cooled rapidly on ice, centrifuged and resuspended in one half volume of a 10 mM NaCl solution on ice. After 30 min on ice the cells were centrifuged and resuspended in a half volume of a 50 mM $CaCl_2$ solution and again incubated for 30 min at 0° C. After centrifugation the cells were resuspended in one tenth volume of a 30 mM $CaCl_2$ solution in 20% glycerol. This competent cell preparation divided in 1 ml aliquots was kept frozen at $-60°$ until needed. For transformation the sample was thawed out on ice and 0.5 ml TEN (0.04 M Tris, pH 8.0, 0.04 m NaCl, 1 mM EDTA) containing 30 mM $CaCl_2$ and the DNA for the transformation (0.1 to 1μg) was added. After 30 min on ice the mixture was heated to 42° C. for 2 min and rapidly cooled on ice. The cells were diluted 1 to 30 in L broth and incubated for two hours at 37° C. to allow expression of rifampicin resistance.

Rifampicin Resistance

The rifampicin resistance was tested on L broth plates containing either 100 μg/ml rifampicin, when plasmid pJC703 was used or 30 μg/ml when plasmid pJC720 was used. The colonies derived after transduction or transformation of pJC720 grow slowly on rifampicin, taking two days at 37° C. to form large colonies. Since rifampicin is light sensitive the plates must be kept dark during this prolonged incubation to prevent growth of background colonies.

Restriction and Ligation Reactions (Cutting and Coupling Reactions

Restriction with HindIII (from Boehringer) was carried out in a medium comprising 30 mM Tris (pH 7.6), 10 mM $MgCl_2$ and 10 mM NaCl to completion. The treatment (digestion) with SalI, EcoRI and BglII were carried out in the same buffer. SalI and EcoRI were gifts from H. Mayer and H. Schütte, and BglII a gift from R. Eichenlaub. The treatment (digestion) with KpnI (from Bio-Labs) was carried out in a medium comprising 10 mM Tris (pH 7.9), 6 mM $MgCl_2$, 6 mM NaCl, 10 mM dithiothreitol and 100 μg/ml bovine serum-albumin.

Gel electrophoresis was carried out in 1% agarose gels; cf. Collins, Current Top. Microbiol. Immunol., 78 (1977) 121–170.

Production of a Packageable Substrate From Plasmid DNA

Plasmid pJC703 (FIG. 1) yields two HindIII restriction fragments: fragment A containing the lambda cos site and the ColEI replicon and fragment B containing the gene for rifampicin resistance (rpoB). It was hoped that cleavage and religation of plasmid pJC703 with HindIII and DNA ligase respectively, would produce a population of polymers which could imitate the natural substrate for packaging. The important features for packaging and cleaving lambda DNA appear to be the occurrence of cos sites about 23 to $33 \times 10^6$ daltons apart; cf. Feiss et. al., Virology, 77 (1977) 281–293. This would be expected to occur in this randomly ligated mix through the generation of molecules such as ABBA, ABBBA, and AABA. Cleavage of such molecules at the cos sites, and subsequent recircularization would lead to the loss of an entire A fragment, thus generating plasmids of the form ABB, ABBB and AAB, respectively.

Analysis of the Plasmids Produced After Packaging and Transduction

After packaging the religated HindIII fragments of pJC703 several thousand rifampicin resistant colonies were obtained by transduction into strain N205 (Experiment 1, Table II). The yield of rifampicin resistant clones is very dependent on the concentration of the vector (cosmid) DNA during the ligation. This supports the hypothesis that efficient packaging is brought about through formation of the long polymers discussed above. In contrast, the formation of such highly polymerised chains is most detrimental to the efficiency of transformation, as has been previously noted; cf. Collins, loc. cit.

Fifty-two colonies were picked at random for further testing. They were all found to be colicin El-resistant and colicin E2 sensitive, indicative of the plasmid-coded E1-immunity carried on the HindIII fragment A. Small cleared-lysates were made from each, and to check the presence and approximate size of the plasmid DNA 5 μl samples (+ sodium dodocyl sulphate to 0.1%) were electrophoresed on Tris-borate 0.8% agarose gels; cf. Collins loc. cit. Supercoiled DNA was prepared from the first twelve samples and, from the remaining 40, from those showing the presence of plasmids larger than pJC703. These DNA's and in some cases the products of a second packaging step were analysed more thoroughly using cleavage with the following restriction enzymes BglII, KpnI, SalI, EcoRI and HindIII.

The majority of plasmids fell into one of the three size classes 17.3 Md, approximately 24 Md, and approximately 29 Md (from electrophoresis of supercoils in agarose gels with pJC703 and pJC802 (25 Md) as molecular weight markers). On digestion with a particular nuclease these larger plasmids yielded the same sized bands as in the original plasmid and one additional band. Apart from this new band, it was noticed that those bands derived from the $HindIII_B$ fragment (B) became more intense relative to those derived from the $HindIII_A$ fragment (A).

The Effect of Size on the Efficiency of Cosmid-Hybrid Packaging

The cosmid pJC703 (17.3 Md) appears to be packaged in vitro with a much lower frequency than its larger hybrid derivatives. The high percentage of packaging of larger hybrids is evidence that this size selection is also occurring for restriction-endonuclease-cleaved and religated DNA. This size dependency was further tested using the cosmid pJC720 (16 Md), which contains a single HindIII site (FIG. 1), to clone fragments from the R factor Rldrd-19 (Exp. 3, Table II). The HindIII fragments of this plasmid are of the following sizes 42.8, 11.5, 2.9, 2.0, 1.95, 1.8, 0.15 and 0.1 Md; Blohm, Proc. 2nd Int. Symp. Microbiol. Drug Resist., Vol. 2, Tokyo 1977. The 11.5 Md fragment carries the gene for ampicillin resistance. 90% of the rifampicin resistant clones tested were found also to be ampicillin resistant, and carrying at least the 11.5 Md HindIII fragment from Rldrd-19, newly inserted. It would seem therefore that a very strong size selection had been imposed in which the 27.5 to 29.5 Md hybrids were packaged and transduced preferentially over the 17 to 18 Md hybrids. By contrast transformation with the same DNA yielded few rifampicin and ampicillin resistant hybrids.

Finally in Experiment 4 (Table II) pJC720 was used to clone fragments from Pseudomonas AM1 chromosomal DNA partially digested with HindIII. Most of the first 32 clones tested carried new DNA fragments of at least 4 Md, up to 14 Md, the majority carrying more than 7 Md. On this basis a few hundred of the clones obtained should constitute a gene bank of Pseudomonas Am 1 chromosomal DNA in *Escherichia coli;* cf. Clarke & Carbon, Cell, 9(1976) 91–99.

With respect to the pel⁻ strain as host the efficiency of DNA injection is dependent on the size of the lambda DNA; cf. Emmons, J. Molec. Biol., 93 (1974) 511–525. As the pel⁻ strain was used as a recipient for the packaged HindIII cleaved and ligated pJC703, an even stronger size-dependence was found. Out of 28 clones tested 19 had plasmids in the 24–25 Md size range and 8 in the 29–30 Md size range, as estimated by gel-electrophoresis of cleared lysates, with a single plasmid of the starting size (17 Md). All of the larger plasmids (23.6 Md and 29.9 Md) were found to be of the form $\overline{ABB}$ or $\overline{ABBB}$ (by cleavage with SalI and EcoRI) as had been found using N205 as recipient.

The Packaging of Cosmid-Hybrids as an Exceptionally Efficient Cloning System for Large DNA Fragments (Comparison with the Transformation System and the Hohn and Murry Transducing System)

We have demonstrated that the packaging of plasmid DNA in lambda bacteriophage particles can be used as a method for obtaining plasmid hybrids in the 20 to 30 Md size range, when using plasmid DNA which has been linked in vitro to foreign DNA fragments. The yield of clones containing these hybrids, particularly for those of the larger size class, is several hundred or thousand fold better than that obtained through normal transformation. Furthermore, by the use of small plasmids which themselves are inefficiently transformed, the background of non-hybrid clones is effectively eliminated in a single step without resort to modification of the DNA substrates or to the elaborate selection or screening procedures normally used in cloning experiments.

The use of the cosmids in this system can be compared favourably with the in vitro packaging of lambda-cloning vectors which has been found to be independent of the size of the DNA in the range 24 to 28 Md (cf. Hohn & Murray, loc. cit.), and in which the normal size-dependent selection for lambda hybrids cannot be imposed unless a second infectious cycle is carried out; with respect to the normal size-dependent selection for lambda hybrids, cf. e.g Thomas et. al., Proc. Nat. Acad. Sci. USA, (1974) 4579–4583; Murray & Murray, Nature, 251 (1974) 476–481; Murray et. al., Molec. Gen. Genet., 150 (1977) 53–61; and Blattner et. al., Science 196 (1977) 161–169. Such a second cycle entails the dangers of producing sibling clones and the selective loss of some hybrids; cf. Cameron et. al., Proc. Nat. Acad. Sci. USA, 72 (1975) 3416–3420. In the range of 24 to 31 Md, however, a size-dependent in vitro packaging system has been described (Sternberg et. al., Gene, 1 (1977) 255–280), but a lower size limit for the vector is set by the requirement for bacteriophage genes for plaque production. This size dependency allowed the formation of a transduced population in which 5 to 10% of all plaques contained hybrid phage; cf. Sternberg et. al., loc. cit. This should be contrasted with the results of experiments 3 and 4 (Table II) in which essentially only hybrids are produced.

Table II (Comparison with the Transformation System)

Transformation and packaging efficiencies of plasmids containing cos sites, before and after cleavage with HindIII and ligation with DNA ligase. Material to be transformed or (subsequent to packaging) transduced was selected for media containing rifampicin. Yields are given as rifampicin resistant colonies per microgram input DNA. In experiment 1, the percentage of hybrid clones, refers to the percent containing more than one copy of the HindIII$_B$ fragment. About 90% of the rifampicin resistant colonies from experiment 3 also contained the HindIII fragment (11 Md) from Rldrd-19 which also carries Ampicillin resistance.

The efficiency of packaging lambda b2 DNA in parallel experiments was about $10^7$–$10^8$ pFU per microgram input DNA.

FIG. 1: Restriction endonuclease map of pJC703 and pJC720. The fragments obtained with each enzyme are alphabetically labelled according to size. Dotted lines indicate the relative positions of the EcoRI cleavage site on each map, and the continuous vertical line the positions on the HindIII cleavage sites. The distances from the HindIII sites to the nearest cleavage sites for each restriction enzyme are indicated in megadaltons (Md). These values are used in the analysis of plasmids containing polymeric HindIII fragments. The ColEI part of these plasmids is actually derived from a freak isolate (pJC309) which contains a SalI site which is not present in ColEI.

TABLE II

| | | | | Transformation | | Packaging and transduction | |
|---|---|---|---|---|---|---|---|
| Experiment | DNA | Molecular weight of the cosmid (Md) | DNA concentration at ligation step | Colonies resistant against rifampicin/ μg DNA (i.e. total colonies = hybrids + non-hybrids) | hybrid (i.e. resistant colonies) (%) | Colonies resistant against rifampicin/ μg DNA (i.e. total colonies = hybrids + non-hybrids) | hybrid (i.e. resistant colonies) (%) |
| 1 | pJC703 × HindIII (2 restriction sites), ligated | 17,3 | 500 | 30 | not tested | $1,0 \times 10^5$; $2,4 \times 10^4$ | about 50 |
| 3 | pJC720 × HindIII (1 restriction site) + Rldrd19 × HindIII | 16 / ligated | 146 / 50 / 17 | $1,4 \times 10^3$ / $4,1 \times 10^2$ | 0,15 | $1,0 \times 10^2$ / $1,8 \times 10^3$; $2,4 \times 10^3$ | about 90 |
| 4 | pJC720 × | 16 | 330 | | | | |

TABLE II-continued

| Experiment | DNA | Molecular weight of the cosmid (Md) | DNA concentration at ligation step | Transformation | | Packaging and transduction | |
|---|---|---|---|---|---|---|---|
| | | | | Colonies resistant against rifampicin/ μg DNA (i.e. total colonies = hybrids + non-hybrids) | hybrid (i.e. resistant colonies) (%) | Colonies resistant against rifampicin/ μg DNA (i.e. total colonies = hybrids + non-hybrids) | hybrid (i.e. resistant colonies) (%) |
| | HindIII (1 restriction site) + Pseudomonas × HindIII | ligated AM1 | 75 | not tested | | $5 \times 10^3$ | about 90 |

We claim:

1. Process for the production of hybrid bacteria, characterized in that
   (a) a hybrid plasmid having only one cos site of a lambda or a lambdoid phage is produced from (1) a bacterial plasmid of not more than 21 Megadaltons and having only one cos site of a lambda or a lambdoid phage and (2) a foreign DNA fragment,
   (b) the resulting hybrid plasmid is packaged with the lysate of a lambda or lambdoid phage and
   (c) the packaging product is transduced into *Escherichia coli* whereby hybrid bacteria are formed.

2. Process according to claim 1, characterized in that a plasmid having only one cut site per restriction endonuclease is cut in the presence of one to two restriction endonucleases and coupled in the presence of a ligase to a hybrid plasmid in step (a).

3. Process according to claims 1 or 2, characterized in that a plasmid having not more than about 18 Megadaltons is used.

4. Process according to claims 1 or 2, characterized in that in step (a) a plasmid is used which has been cut in the presence of a restriction endonuclease only at one site and which has been coupled with a DNA fragment which can be cut in step (a) in the presence of a different restriction endonuclease at one site only.

* * * * *